United States Patent
Morita

(10) Patent No.: US 10,174,357 B2
(45) Date of Patent: Jan. 8, 2019

(54) METHOD AND KIT FOR QUANTIFYING CARDIOLIPIN

(71) Applicant: SHIGA UNIVERSITY OF MEDICAL SCIENCE, Otsu-shi, Shiga (JP)

(72) Inventor: Shin-ya Morita, Otsu (JP)

(73) Assignee: SHIGA UNIVERSITY OF MEDICAL SCIENCE, Otsu-shi, Shiga (JP)

(*) Notice: Subject to any disclaimer, the term of this patent is extended or adjusted under 35 U.S.C. 154(b) by 171 days.

(21) Appl. No.: 15/301,133

(22) PCT Filed: Mar. 17, 2015

(86) PCT No.: PCT/JP2015/057870
§ 371 (c)(1),
(2) Date: Dec. 13, 2016

(87) PCT Pub. No.: WO2015/151801
PCT Pub. Date: Oct. 8, 2015

(65) Prior Publication Data
US 2017/0114387 A1  Apr. 27, 2017

(30) Foreign Application Priority Data
Apr. 3, 2014 (JP) ................. 2014-077076

(51) Int. Cl.
| | |
|---|---|
| C12Q 1/28 | (2006.01) |
| C12Q 1/26 | (2006.01) |
| C12Q 1/32 | (2006.01) |
| C12Q 1/44 | (2006.01) |
| C12Q 1/48 | (2006.01) |
| G01N 21/64 | (2006.01) |
| G01N 33/92 | (2006.01) |

(52) U.S. Cl.
CPC ............. *C12Q 1/28* (2013.01); *C12Q 1/26* (2013.01); *C12Q 1/32* (2013.01); *C12Q 1/44* (2013.01); *C12Q 1/485* (2013.01); *C12Y 101/03021* (2013.01); *C12Y 111/01007* (2013.01); *C12Y 207/0103* (2013.01); *C12Y 301/04004* (2013.01); *G01N 21/6428* (2013.01); *G01N 33/92* (2013.01); *G01N 2333/902* (2013.01); *G01N 2333/908* (2013.01); *G01N 2333/916* (2013.01); *G01N 2333/91215* (2013.01); *G01N 2405/04* (2013.01)

(58) Field of Classification Search
CPC ... C12N 1/20; C12N 1/00; C12N 1/04; C12Q 1/28; C12Q 1/32; C12Q 1/44; C12Q 1/485; C12Y 101/03021; C12Y 111/01007; C12Y 207/0103; C12Y 301/04004; G01N 21/6428; G01N 2333/902; G01N 2333/908; G01N 2333/91215; G01N 2333/916; G01N 2405/04; G01N 33/92
See application file for complete search history.

(56) References Cited

FOREIGN PATENT DOCUMENTS

| | | |
|---|---|---|
| JP | 2013-255436 A | 12/2013 |
| WO | 2012/070617 A1 | 5/2012 |

OTHER PUBLICATIONS

International Search Report dated Jun. 16, 2016 from International Application No. PCT/JP2015/057870, including english translation, 4 pages total.
Fuller et al., "Determination of the cardiolipin content of individual mitochondria by capiliary electrophoresis with laser-induced fluorescence detection", Electrophoresis, 2002, vol. 23, No. 11, pp. 1571-1576.
Garrett et al., "Quantification of cardiolipin molecular species in *Escherichia coli* lipid extracts using liquid chromatography/electrospray ionization mass spectrometry", Rapid Communications in Mass Spectrometry, 2012, vol. 26, No. 19, pp. 2267-2274.
Leung et al., "Superior Fluorescent Probe for Detection of Cardiolipin", Analytical Chemistry, Jan. 2014, vol. 86, No. 2, pp. 1263-1268.
Morita et al., "Enzymatic measurement of phosphatidic acid in cultured cells", Journal of Lipid Research, 2009, vol. 50, No. 9, pp. 1945-1952.
Morita et al., "Specific and sensitive enzymatic measurement of sphingomyelin in cultured cells", Chemistry and Physics of Lipids, 2012, vol. 165, No. 5, pp. 571-576.
Morita et al., "Enzymatic measurement of phosphatidylserine in cultured cells", Journal of Lipid Research, 2012, vol. 53, No. 2, pp. 325-330.
Morita et al., "Functional analysis of two isoforms of phosphatidylethanolamine N-methyltransferase", Biochemical Journal, 2010, vol. 432, No. 2, pp. 387-398.
Morita et al., "Quantification of Total Phosphatidylglycerol and Cardiolipin in Cells by an Enzymatic Fluorometric Method", Proceedings of Japanese Conference on the Biochemstry of Lipids, May 2014, vol. 56, pp. 126-128, with 2 pages of English translation and presentation by inventor at conference on Jun. 7, 2014.
Morita et al., "Novel Enzyme-based fluorometric method for measuring phosphatidylglycerol and cardiolipin", Proceedings of 8th Young Investigators Symposium on Clinical Pharmaceutical Sciences, Nov. 2014, p. 74 and presentation by inventor at the symposium on Nov. 16, 2014.
Morita et al., "Development of Phosphatidylglycerol/Cardiolipin Enzymatic Fluorometric Measurement", Proceedings of 36th Symposium on Biomembrane-Drug Interaction, 2014, pp. 29-30, with 4 pages of English translation (published online Oct. 8, 2014) and presentation by the inventor at the symposium on Nov. 20, 2014.

*Primary Examiner* — Deborah K Ware
(74) *Attorney, Agent, or Firm* — MH2 Technology Law Group, LLP

(57) ABSTRACT

A method for quantifying cardiolipin in a sample, comprises the steps of: (1) treating the sample with phospholipase D, glycerol kinase, glycerol-3-phosphate oxidase, and peroxidase and (2) measuring the fluorescence intensity, absorbance, or luminescence intensity of a compound generated in step (1) to quantify cardiolipin using a calibration curve obtained beforehand; and a kit for quantifying cardiolipin comprises phospholipase D, glycerol kinase, glycerol-3-phosphate oxidase, and peroxidase.

7 Claims, 2 Drawing Sheets

METHOD AND KIT FOR QUANTIFYING CARDIOLIPIN

TECHNICAL FIELD

The present invention relates to a method for quantifying cardiolipin and a kit for quantifying cardiolipin.

BACKGROUND ART

Cardiolipin (hereinafter sometimes referred to as CL) is a kind of phospholipid, and is widely distributed in animals, plants, and bacteria. Cardiolipin accounts for 1 to 15% of total phospholipids in animals and plants, and 50% of total phospholipids in some bacteria. Cardiolipin has the following structure,

[Chem. 1]

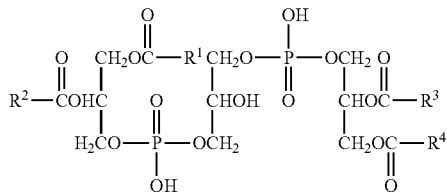

wherein $R^1$, $R^2$, $R^3$, and $R^4$ each represent a chain hydrocarbon group.

CL is a phospholipid mainly present in mitochondria in mammalian cells. CL therefore controls various enzyme activities present in mitochondria that include an electron transfer system, and takes part in apoptosis. In particular, a large amount of CL is contained in a cardiac muscle cell.

Conventionally, CL is quantified using a thin-layer chromatography and a phosphorus quantification method. However, these methods exhibit low detection sensitivity and low quantification accuracy, and require time and effort. Mass spectrometry for CL has not been established.

Thus, although CL is an important and essential component in the body, analysis methods thereof are extremely scarce even today.

The present inventors have developed enzymatic fluorometric measurements for phospholipids (phosphatidylcholine, phosphatidylethanolamine, phosphatidic acid, phosphatidylserine, and sphingomyelin) (Patent Literature 1 and 2).

Patent Literature 1 reports an enzymatic quantification method of phosphatidylserine in which the fluorescence intensity of a compound produced by treating a sample with phospholipase D, L-amino-acid oxidase and peroxidase is measured.

Patent Literature 2 reports an enzymatic quantification method of sphingomyelin in which the fluorescence intensity of a compound produced by treating a sample with sphingomyelinase, alkaline phosphatase, choline oxidase, and peroxidase is measured.

However, since an enzymatic quantification method of CL has not been developed, an inability to determine the profile of all phospholipid classes by excluding CL is a problem.

CITATION LIST

Patent Literature

PTL 1: WO2012/070617
PTL 2: Japanese Application No. 2013-255436

SUMMARY OF INVENTION

Technical Problem

Thus, CL is conventionally quantified by thin-layer chromatography/phosphorous quantification methods. However, these methods have disadvantages in that the detection sensitivity and quantification accuracy are low, and time and effort are required.

An object of the present invention is to provide a method for quantifying cardiolipin (CL) conveniently with high sensitivity, and a kit for quantifying cardiolipin.

Solution to Problem

The present inventors conducted extensive research to achieve the above object and found that the above object can be achieved by using a series of enzyme reactions shown in FIG. 1. The method for quantifying cardiolipin shown in FIG. 1 is explained below.

(i) CL is hydrolyzed by phospholipase D to produce glycerol and phosphatidic acid.
(ii) Glycerol is phosphorylated by glycerol kinase to produce glycerol-3-phosphate.
(iii) Glycerol-3-phosphate is oxidized by glycerol-3-phosphate oxidase to produce $H_2O_2$.
(iv) 10-Acetyl-3,7-dihydroxy phenoxazine (Amplex (tradename) Red) are reacted with $H_2O_2$ by peroxidase to produce resorufin. The CL content can be measured by measuring the fluorescence intensity of resorufin.

It was not known that phospholipase D can hydrolyze CL to release glycerol as above.

Based on these findings, the present invention was accomplished as a result of further examination. The present invention provides the following method and kit for quantifying cardiolipin.

(I) Method for Quantifying Cardiolipin
(I-1) A method for quantifying cardiolipin in a sample, comprising the steps of:
 (1) treating the sample with phospholipase D, glycerol kinase, glycerol-3-phosphate oxidase, and peroxidase and
 (2) measuring the fluorescence intensity, absorbance, or luminescence intensity of a compound generated in step (1) to quantify cardiolipin using a calibration curve obtained beforehand.
(I-2) The method according to Item (I-1), wherein in step (1), the sample is treated with enzymes in two steps:
 (a) a step of treating with phospholipase D, and
 (b) a step of treating with glycerol kinase, glycerol-3-phosphate oxidase, and peroxidase.
(I-3) The method according to Item (I-1) or (I-2) wherein the phospholipase D is derived from a microorganism belonging to the genus *Streptomyces*.
(I-4) The method according to any of Items (I-1) to (I-3) wherein the phospholipase D is derived from a microorganism belonging to *Streptomyces chromofuscus*.
(II) Kit for Quantifying Cardiolipin
(II-1) A kit for quantifying cardiolipin comprising phospholipase D, glycerol kinase, glycerol-3-phosphate oxidase, and peroxidase.

(II-2) The kit according to Item (II-1) wherein the phospholipase D is derived from a microorganism belonging to the genus *Streptomyces*.
(II-3) The kit according to Item (II-1) or (II-2) wherein the phospholipase D is derived from a microorganism belonging to *Streptomyces chromofuscus*.

Advantageous Effects of Invention

The method and kit for quantifying cardiolipin of the present invention can quantify cardiolipin with high sensitivity and high accuracy.

The detection limit of the present invention is 10 pmol, which is extremely highly sensitive compared to conventional CL quantification methods. This enables highly accurate quantification.

Further, the main necessary procedures of the present invention are pipetting of samples and reaction solutions into a microplate, and it is very simple. This enables high-throughput quantification.

DESCRIPTION OF EMBODIMENTS

Figure 1:
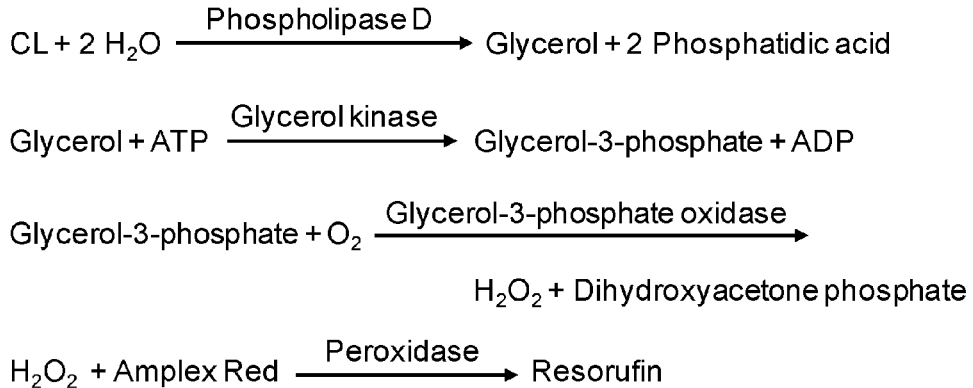
FIG. 1 shows reactions in the CL quantification method of the present invention.

The method and kit for quantifying cardiolipin of the present invention are explained in detail below.
Method for Quantifying Cardiolipin The method for quantifying cardiolipin in a sample according to the present invention comprises the following steps:
(1) treating the sample with phospholipase D, glycerol kinase, glycerol-3-phosphate oxidase, and peroxidase, and
(2) measuring the fluorescence intensity, absorbance, or luminescence intensity of a compound generated in step (1) to quantify cardiolipin using the calibration curve obtained beforehand.

Each step is explained below.
Step (1)

In Step (1), a sample is treated with phospholipase D, glycerol kinase, glycerol-3-phosphate oxidase, and peroxidase.

By treating the sample with phospholipase D, glycerol and phosphatidic acid are produced from CL and $H_2O$. Subsequently, by treating the resulting product with glycerol kinase, glycerol-3-phosphate and ADP (adenosine 5'-diphosphate) are produced from glycerol and ATP (adenosine 5'-triphosphate). Then, by treating the resulting product with glycerol-3-phosphate oxidase, $H_2O_2$ and dihydroxyacetone phosphate are produced from glycerol-3-phosphate and $O_2$.

Phospholipase D (EC 3.1.4.4) is a phospholipid hydrolytic enzyme that hydrolyzes the phosphodiester linkage of a glycerophospholipid between the phosphorus and the base group. As phospholipase D used in the present invention, phospholipase D derived from any of microorganisms, animals, and plants can be used as long as it hydrolyzes cardiolipin to produce glycerol and phosphatidic acid. Phospholipase D derived from microorganisms is preferable, phospholipase D derived from the genus *Sterptomyces* is more preferable, and phospholipase D derived from *Streptomyces chromofuscus* is particularly preferable.

As glycerol kinase (EC 2.7.1.30) used in the present invention, glycerol kinase derived from microorganisms, animals, and plants can be widely used as long as it phosphorylates glycerol to produce glycerol-3-phosphate. Of these, glycerol kinase derived from microorganisms is preferable, and glycerol kinase derived from *Cellulomonas* sp. is particularly preferable.

As glycerol-3-phosphate oxidase (EC 1.1.3.21) used in the present invention, glycerol-3-phosphate oxidase derived from microorganisms, animals, and plants can be widely used as long as it oxidizes glycerol-3-phosphate to produce hydrogen peroxide. Of these, glycerol-3-phosphate oxidase derived from microorganisms is preferable, and glycerol-3-phosphate oxidase derived from *Pediococcus* sp. is particularly preferable.

As peroxidase (EC 1.11.1.7) used in the present invention, peroxidase derived from microorganisms, animals, and plants can be widely used. Of these, peroxidase derived from plants is preferable, and peroxidase derived from horseradish is particularly preferable.

In the method for quantifying CL of the present invention, to treat a sample with the above four enzymes, the four enzymes may be added to the sample together at the same time or may be added to the sample sequentially. However, the sample is preferably treated with enzymes in two steps: (a) phospholipase D, and (b) glycerol kinase, glycerol-3-phosphate oxidase, and peroxidase. Treating the sample with the four enzymes in such steps improves the accuracy.

The conditions in which a sample is treated with phospholipase D can be suitably determined according to the properties of the enzyme to be used. The pH is generally 6 to 9, and the temperature is generally 15 to 40° C. The time for which the sample is treated with phospholipase D can be determined according to the properties of the sample to be analyzed; however, it is generally one minute or more.

The conditions in which a sample is treated with glycerol kinase can be suitably determined according to the properties of the enzyme to be used. The pH is generally 6 to 9 and the temperature is generally 15 to 40° C. The time for which the sample is treated with glycerol kinase can be determined according to the properties of the sample to be analyzed; however, it is generally one minute or more.

The conditions in which a sample is treated with glycerol-3-phosphate oxidase can be suitably determined according to the properties of the enzyme to be used. The pH is generally 6 to 9 and the temperature is generally 15 to 40° C. The time for which the sample is treated with glycerol-3-phosphate oxidase can be determined according to the properties of the sample to be analyzed; however, it is generally one minute or more.

The conditions in which a sample is treated with peroxidase can be suitably determined according to the properties of the enzyme to be used. The pH is generally 6 to 9 and the temperature is generally 15 to 40° C. The time for which the sample is treated with peroxidase can be determined according to the properties of the sample to be analyzed; however, it is generally one minute or more.

When the reaction temperature and pH of the four enzymes are the same, all of the enzyme reactions can be performed at the same time. When the reaction temperature and pH are different between enzymes, the required temperature and pH are sequentially adjusted in steps to perform reaction.

In the method for quantifying CL of the present invention, the amounts of the four enzymes in the reaction solution in which a sample is treated with the four enzymes can be suitably adjusted to amounts suitable for analysis considering the amount of CL contained, etc. Since high accuracy is attained by completing the reaction of these four enzymes almost perfectly within the reaction time, it is preferable to use sufficient amounts of enzymes.

In the present invention, the reaction solution for treating a sample with phospholipase D, glycerol kinase, glycerol-3-phosphate oxidase, and peroxidase contains a compound that increases the fluorescence intensity, absorbance, or luminescence intensity by the reaction with $H_2O_2$ in the presence of peroxidase. When the four enzymes are sequentially reacted, the compound may be contained at least in the reaction solution for reacting peroxidase. Examples of the compound include 10-acetyl-3,7-dihydroxy phenoxazine (Amplex Red). The concentration of 10-acetyl-3,7-dihydroxy phenoxazine in the reaction solution can be suitably adjusted; however, it is generally 10 to 500 µM.

The reaction solution for treating a sample with phospholipase D, glycerol kinase, glycerol-3-phosphate oxidase, and peroxidase may contain, in addition to the sample and enzymes, a buffer solution, metal salt, ATP, or the like. Examples of the buffer solution include tris-hydrochloric acid buffer solutions, potassium phosphate buffer solutions, glysine-hydrochloric acid buffer solutions, acetic acid buffer solutions, citrate buffer solutions, and the like. Examples of the metal salt include magnesium salt, potassium salt, sodium salt, and the like. The reaction solution for treating a sample with glycerol kinase preferably contains ATP and magnesium salt.

The sample used in the present invention is not particularly limited as long as the quantification of CL is required. Examples of the sample include cultured cells, culture media, human or animal tissues and body fluids including blood, plant tissues and plant fluids, fungi, bacteria and bacteria culture media, medicines, foods, supplements, and the like. The sample may be diluted with a diluted solution, and examples of the diluted solution include buffer solutions. Examples of the buffer solution are those described above. The sample may be pre-treated before enzyme reaction, for example, by heating, etc.

Step (2)

In Step (2), the fluorescence intensity, absorbance, or luminescence intensity of the compound produced in Step (1) is measured to quantify cardiolipin using the calibration curve obtained beforehand.

Since one $H_2O_2$ molecule is generated from one CL molecule as a result of a series of reactions, CL can be quantified by measuring the amount of $H_2O_2$.

Specific examples of the measurement method in Step (2) include a method for measuring absorbance using a compound (e.g., N,N'-bis(2-hydroxy-3-sulfopropyl)tolidine) that reacts with $H_2O_2$ by peroxidase to show a new absorption wavelength, a method for measuring absorbance using compounds that react with $H_2O_2$ by peroxidase to perform oxidization condensation and to show a new absorption wavelength (e.g., oxidization condensation of phenol and 4-amino antipyrin), a method for measuring fluorescence intensity using a compound (e.g., 10-acetyl-3,7-dihydroxyphenoxazine) that reacts with $H_2O_2$ by peroxidase to newly produce fluorescence, and a method for measuring the intensity of luminescence using a compound (e.g., luminol) that reacts with $H_2O_2$ by peroxidase to newly produce luminescence.

Of the above methods, a method for measuring fluorescence intensity using a compound that reacts with $H_2O_2$ by peroxidase to newly produce fluorescence is preferable, and a method for measuring the fluorescence intensity of resorufin generated by reacting 10-acetyl-3,7-dihydroxy phenoxazine (Amplex Red) with $H_2O_2$ by peroxidase is particularly preferable. Resorufin is a fluorescent compound, and has a maximum excitation wavelength of 571 nm and a maximum emission wavelength of 585 nm. In contrast, 10-acetyl-3,7-dihydroxy phenoxazine is a non-fluorescent compound, and fluorescence is not generated even when it is irradiated by light with a wavelength of about 571 nm. Since one resorufin molecule is generated from one CL molecule as a result of a series of reactions, CL can be quantified by measuring the amount of resorufin. The amount of resorufin can be determined by measuring the fluorescence intensity using, for example, a fluorescence microplate reader, at an excitation wavelength of 544 nm and an emission wavelength of 590 nm.

In the present invention, examples of the enzymes from microorganisms, animals, or plants widely include enzymes produced from microorganisms, animals, or plants, and their mutants that are obtainable by substitution, addition, deletion, or insertion of one or more amino acids in the amino acid sequence of the enzyme, and that have native enzymatic activities.

The range of "one or more" mentioned above is not particularly limited; however, it is for example 1 to 50, preferably 1 to 25, more preferably 1 to 12, even more preferably 1 to 9, and particularly preferably 1 to 5. The technique for substituting, deleting, or adding one or more amino acids in a specific amino acid sequence is known.

The enzymes mentioned above are commercially available from the market, or can be produced by obtaining the gene according to known gene sequence information and making transformants. The produced enzyme can be purified by affinity chromatography, ion exchange chromatography, hydroxyapatite column chromatography, ammonium sulfate precipitation, etc.

The following is one example of the method for quantifying CL of the present invention. First, the standard samples are prepared by adequately diluting solutions of known CL concentrations, and their fluorescence intensities are measured by the method of the present invention to obtain a calibration curve in response to CL concentration. The fluorescence intensity of a sample with an unknown CL content is then measured using the present invention. The CL content can be determined using the calibration curve.

The method for quantifying cardiolipin of the present invention can quantify cardiolipin with high sensitivity and high accuracy.

Kit for Quantifying Cardiolipin

The kit for quantifying cardiolipin of the present invention comprises phospholipase D, glycerol kinase, glycerol-3-phosphate oxidase, and peroxidase.

By performing the method for quantifying CL using the kit for quantifying CL of the present invention, cardiolipin can be quantified with high sensitivity and high accuracy.

As a method using a kit for quantifying CL of the present invention, the method for quantifying CL as described above can be used.

Phospholipase D, glycerol kinase, glycerol-3-phosphate oxidase, and peroxidase are the same as those described above.

The kit for quantifying CL of the present invention may contain phospholipase D, glycerol kinase, glycerol-3-phosphate oxidase, and peroxidase as enzyme solutions or dry powders. The kit for quantifying CL of the present invention may contain a compound that produces a compound with measurable fluorescence intensity, absorbance, or luminescence intensity by reacting with $H_2O_2$ in the presence of peroxidase. The kit for quantifying CL of the present invention may also contain a buffer solution, metal salt, ATP, etc., and the kit preferably contains at least magnesium salt and ATP. Examples of the buffer solution and metal salt include those described above. It is preferable that the buffer and metal salt are contained in the kit as aqueous solutions or powders.

EXAMPLES

The following Examples describe the present invention in further detail. However, the present invention is not limited thereto.

Material

Phospholipase D derived from *Streptomyces chromofuscus* was purchased from Asahi Kasei Corporation. Glycerol kinase derived from *Cellulomonas* sp. and glycerol-3-phosphate oxidase derived from *Pediococcus* sp. were purchased from Toyobo Co., Ltd. Peroxidase derived from horseradish roots was purchased from Oriental Yeast Co., Ltd. An Amplex Red reagent was purchased from Invitrogen. CL derived from bovine heart and TOCL were purchased from Avanti Polar Lipids, Inc. Other chemicals used were of the highest reagent grade.

Enzymatic Measurement of CL

Measurement was performed using a four-reaction reagent system. Reagent L1 contains 5 U/mL phospholipase D, 1.5 mM $CaCl_2$, 50 mM NaCl, and 50 mM Tris-HCl (pH 7.4). Reagent L2 contains 5 U/mL glycerol kinase, 4.5 mM ATP, 5 U/mL glycerol-3-phosphate oxidase, 5 U/mL peroxidase, 300 μM Amplex Red, 0.2% (v/v) Triton X-100, 1.5 mM $MgCl_2$, 50 mM NaCl, and 50 mM Tris-HCl (pH 7.4). The Amplex Red Stop reagent was purchased from Invitrogen. A CL standard solution was prepared by dissolving CL derived from bovine heart in a 1% (v/v) Triton X-100 aqueous solution.

A sample (10 μL) or a CL standard solution was added to reagent L1 (40 μL), and incubated for 30 minutes at 37° C. After incubation, reagent L2 (50 μL) was added. After incubation for 30 minutes at room temperature, the Amplex Red Stop reagent (20 μL) was added. The fluorescence intensity was measured using a fluorescence microplate reader (Infinite M200, Tecan Japan Co., Ltd.), and the excitation wavelength and the emission wavelength were set at 544 nm and 590 nm, respectively.

Measurement of CL Content in Cells

HEK293 cells were cultured in DMEM containing 10% heat-inactivated FBS in a humidified incubator (5%, $CO_2$) at 37° C. The cells were seeded in 100-mm dishes, and incubated at 37° C. for a few days. After incubation, the cells were chilled on ice, washed, and scraped with cold PBS. The cells were sonicated for disruption. The cellular lipids were extracted by the method of Bligh and Dyer (Bligh, E. G., Dyer, W. J., 1959. A rapid method of total lipid extraction and purification. Can J Biochem Physiol 37, 911-917), and dissolved in 1% (v/v) Triton X-100 prepared just before use. CL in the lipid extract from the cells was measured by the enzymatic quantification method of the present invention.

Results

Test Example 1: CL Measurement

Figure 2:
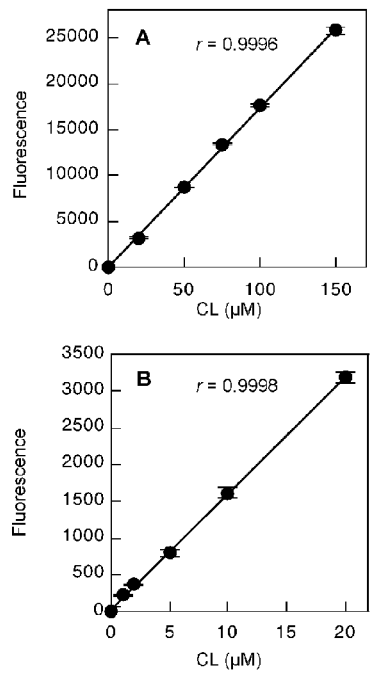
FIG. 2 shows graphs each showing a standard curve for CL measurement of Test Example 1. Each point represents the mean±S.D. of three measurements. The line was obtained by linear regression analysis. The correlation coefficients were r=0.9996 (A) and r=0.9998 (B).

A calibration curve was obtained by using CL standard solutions according to the enzymatic quantification method of CL described above. The results are shown in FIG. 2.

The calibration curve for CL measurement was linear between 0 to 150 μM (r=0.9996: FIG. 2A, R=0.9998: FIG. 2B). The detection limit was 1 μM (10 pmol in the reaction solution).

Figure 3:
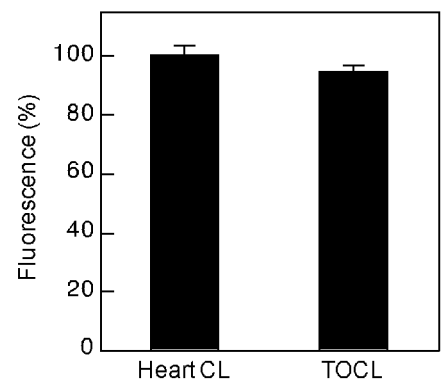
FIG. 3 is a graph showing a fluorescence change in response to CL derived from bovine heart and CL having four oleoyl chains (TOCL) (both 100 μM) in CL measurement of Test Example 1. The fluorescence change of CL derived from bovine heart is represented as 100%. Each bar represents the mean±S.D. of three measurements. Multiple comparison was performed using the Bonferroni test following ANOVA. There was no statistically significant difference between CL derived from bovine heart and TOCL.

The fluorescence intensities of two types of CL were examined at the same concentration (100 μM) according to the enzymatic quantification method of CL described above. FIG. 3 shows the results in which the fluorescence intensity of CL derived from bovine heart is represented as 100%. The comparison between CL derived from bovine heart and TOCL having four oleoyl chains did not show a difference in fluorescence intensity at the same concentration.

Test Example 2: Measurement of CL in Cultured Cells

To confirm the accuracy of CL measurement, a known amount of CL was added to the cellular lipid extract to perform a recovery test (Table 1). As a result, almost 100% of the added CL was collected at each addition amount. The results indicate that other cellular extracts do not interfere with the quantification of added CL, and that the quantification method of the present invention is accurate.

TABLE 1

| Addition amount of CL (μM) | Measurement amount (μM) | Expected amount (μM) | Recovery rate (%) |
|---|---|---|---|
| 0 | 36.43 | | |
| 12.5 | 48.86 | 48.93 | 99.85 |
| 25.0 | 61.25 | 61.43 | 99.70 |
| 50.0 | 87.74 | 86.43 | 101.52 |
| 75.0 | 110.02 | 111.43 | 98.74 |
| 100.0 | 138.06 | 136.43 | 101.19 |

The invention claimed is:

1. A method for quantifying cardiolipin in a sample, comprising the steps of:
   (1) treating the sample in a container with biologically pure phospholipase D, glycerol kinase, glycerol-3-phosphate oxidase, and peroxidase and
   (2) measuring the fluorescence intensity, absorbance, or luminescence intensity of a compound generated in step (1) to quantify cardiolipin using a calibration curve obtained beforehand.

2. The method according to claim 1, wherein in step (1), the sample is treated with enzymes in two steps:
   (a) a step of treating with biologically pure phospholipase D and
   (b) a step of treating with glycerol kinase, glycerol-3-phosphate oxidase, and peroxidase.

3. The method according to claim 1, wherein the biologically pure phospholipase D is derived from a microorganism belonging to the genus *Streptomyces*.

4. The method according to claim 1, wherein the biologically pure phospholipase D is derived from a microorganism belonging to *Streptomyces chromofuscus*.

5. A kit for quantifying cardiolipin comprising:
(a) a container; and
(b) biologically pure phospholipase D, glycerol kinase, glycerol-3-phosphate oxidase, and peroxidase.

6. The kit according to claim 5, wherein the biologically pure phospholipase D is derived from a microorganism belonging to the genus *Streptomyces*.

7. The kit according to claim 5, wherein the biologically pure phospholipase D is derived from a microorganism belonging to *Streptomyces chromofuscus*.

* * * * *